United States Patent
Moritz et al.

(10) Patent No.: US 7,231,810 B2
(45) Date of Patent: Jun. 19, 2007

(54) SEMICONDUCTOR TYPE HYDROGEN SENSOR, DETECTION METHOD AND HYDROGEN DETECTING DEVICE

(75) Inventors: Werner Moritz, Berlin (DE); Jan Szeponik, Berlin (DE)

(73) Assignee: Humboldt-Universitaet zu Berlin, Berlin (DE)

( * ) Notice: Subject to any disclaimer, the term of this patent is extended or adjusted under 35 U.S.C. 154(b) by 104 days.

(21) Appl. No.: 11/209,747

(22) Filed: Aug. 24, 2005

(65) Prior Publication Data
US 2006/0042354 A1 Mar. 2, 2006

Related U.S. Application Data

(60) Provisional application No. 60/651,466, filed on Aug. 26, 2004.

(51) Int. Cl.
*G01N 7/16* (2006.01)
(52) U.S. Cl. .............. 73/31.06; 73/31.05; 73/23.2
(58) Field of Classification Search ........... 73/31.06, 73/23.2, 31.05
See application file for complete search history.

(56) References Cited

U.S. PATENT DOCUMENTS

| | | | |
|---|---|---|---|
| 4,743,954 A * | 5/1988 | Brown ................ | 257/253 |
| 4,795,968 A | 1/1989 | Madou et al. | |
| 4,836,012 A | 6/1989 | Doty et al. | |
| 5,856,780 A | 1/1999 | McGeehin | |
| 6,165,336 A * | 12/2000 | Maki et al. ............ | 204/415 |
| 6,284,577 B1 * | 9/2001 | Suzawa et al. ........ | 438/163 |
| 6,468,843 B2 * | 10/2002 | Suzawa et al. ........ | 438/151 |
| 7,001,446 B2 * | 2/2006 | Roark et al. .......... | 95/56 |
| 2002/0187583 A1 | 12/2002 | Chang et al. | |
| 2006/0055392 A1 * | 3/2006 | Passmore et al. ..... | 324/71.1 |

FOREIGN PATENT DOCUMENTS

| | | |
|---|---|---|
| DE | 294 797 A5 | 10/1991 |
| DE | 43 32 138 A1 | 3/1995 |
| JP | 62250352 | 10/1987 |

OTHER PUBLICATIONS

Moritz et al., "All solid state room temperature hydrogen sensor", Meeting Abstracts: 2004, Joint International Meeting—206th, Meeting of the Electrochemical Society/2004 Fall Meeting of the Electrochemical Society of Japan, Feb. 2004, p. 2564.

Bartholomaeus et al., "Semiconductor sensors for fluorine detection—optimization for low and high concentrations", Sensors and Actuators B 65 (2000), pp. 270-272.

Moritz et al., "Hydrogen Sensitivity of a Mis-Structure Based on the PT/LAF$_3$ Interface", Abstract, Published on a conference which took place in Brazil from Aug. 31 to Sep. 9, 2003.

* cited by examiner

*Primary Examiner*—Hezron Williams
*Assistant Examiner*—Rodney Frank
(74) *Attorney, Agent, or Firm*—Rothwell, Figg, Ernst & Manbeck, P.C.

(57) ABSTRACT

The invention relates to a high sensitive semiconductor type hydrogen sensor, an alarm of hydrogen which incorporates this sensor and a method of sensing hydrogen concentrations by using this sensor.

19 Claims, 5 Drawing Sheets

SEMICONDUCTOR TYPE HYDROGEN SENSOR, DETECTION METHOD AND HYDROGEN DETECTING DEVICE

CROSS REFERENCE TO RELATED APPLICATION

This application claims the benefit of U.S. Provisional 60/651,466, filed Aug. 26, 2004.

FIELD OF THE INVENTION

The main object of the present invention relates to a high sensitive hydrogen thin film sensor 1 working at room temperature and hence, requiring low power consumption. Due to the semiconductor structure the sensor can be produced cost-effective. The invention also relates to an alarm of hydrogen which incorporates this sensor and to a method of sensing hydrogen concentrations by using this sensor as capacitive semiconductor sensor, gate region of field effect transistor (FET) or sensor based on the photoeffect in the semiconductor. The sensor is aimed at fire detection measuring reliably the small hydrogen concentrations occuring in the event of fire and raising the alarm considerably earlier than known smoke detectors. Besides, the hydrogen sensor may be usefully employed for process control in plants or in environment protection,

DESCRIPTION OF THE PRIOR ART

Hydrogen gas is used in variety of applications ranging from semiconductor thin film processing to rocket fuel in the aerospace industry. The combustible nature of hydrogen however, makes its detection vitally important.

Hydrogen is also known as a gas being suitable for detecting fire. Thus, U.S. Pat. No. 5,856,780 describes a fire detector which is responsive to an increase in parameters indicative of a fire, namely the atmospheric concentrations of carbon monoxide, hydrogen and water vapor. U.S. Pat. No. 4,088,986 discloses a system for sensing smoke and fire which is capable of sensing the presence of hydrogen and hydrocarbon vapors such as methane and propane.

Hydrogen gas sensors are known in manifold constructive embodiments and with different working principles. Lundström described at the first time in Appl. Phys. Lett., 26 (1975), p. 55–57 a silicon based metal/insulator/semiconductor (MIS) structure for detecting hydrogen. The sensor is driven at temperatures about 140° C. Its behaviour at room temperature is instable. Besides silicon semiconductors like SiC or GaN/AlGaN heterostructures also have been used at temperatures from 400 to 600° C. U.S. Pat. No. 6,265,222 and U.S. Pat. No. 6,596,236 describe microstructures with hotplates for selectively heating the hydrogen gas sensor element according to a pre-determined time-temperature program.

It would be a significant advance in the art to provide a hydrogen sensor not requiring an increase of temperature for its operation.

It therefore is one object of the present invention to provide a hydrogen sensor that works at room temperature realizing a low power consumption and low production cost.

It is another object of the invention to provide a hydrogen sensor that senses the presence of hydrogen early and in a reliable and reproducible manner.

It is yet another object of the present invention to provide a stable hydrogen sensor with high sensivity that does not change with change of the relative humidity of air, that means a hydrogen sensor with stable long time behaviour.

It is another object of the invention to provide a hydrogen sensor which can be used for fire detection.

SUMMARY OF THE INVENTION

To achieve the above objectives, a hydrogen sensor of the present invention which is driven at room temperature is a hydrogen thin film sensor 1 comprising a semiconductor substrate 2, a thin film insulating layer 3, a thin film fluoride ion conducting layer 4, a thin metal film of a first electrode 5 and a thin metal film of a second electrode 6, wherein the insulating layer 3 is formed on the semiconductor substrate 2, the fluoride ion conducting layer 4 is formed on the insulating layer 3, the metal film of the first electrode 5 is formed on the fluoride ion conducting layer 4 and the metal film of the second electrode 6 is formed on the back of the semiconductor substrate 2.

In a preferred embodiment of the invention the first electrode 5 or the secsond electrode 6 or both are accomplished as resistive heating elements for reactivation of the sensor 1, if the response time increases with continous use. A termal treatment which can be done simply and fast by using these electrodes as resistive heaters was shown to reactivate the sensor. The termal treatment can be repeated without limitation leading to a stable long time behaviour of sensor 1. The reactivation is realized out of the hydrogen measurements by applying a voltage to electrodes 5 and/or 6. For that purpose electrodes 5 and/or 6 have two temperature stable and electroconductive contacts 7 and 8.

According to the invention it is preferred to heat the thin metal electrode 5, which is in an especially preferred embodiment of the invention a palladium electrode. Short heating pulses from 10 μs up to maximum 2 minutes have been proven to be sufficient for reactivation of the hydrogen sensor 1. It has been found, surprisingly, that even temperatures smaller than 300° C., preferably from 110° C. to 280° C., are sufficient for reactivation. The reactivation of the hydrogen sensor 1 of the invention has shown to be necessary in an interval from 2 hours up to 7 days.

Heating the thin metal electrode 5 has the advantage that only the $H_2$-sensitive interface, which is the fluoride ion conducting layer/electrode 5—interface that requires reactivation, is heated. This way the small temperature rise of the semiconductor substrate ensures rapid cooling and the hydrogen measurements can be continued immediately after reactivation.

Therefore, the invention also relates to a method of reactivating the hydrogen sensor 1 by short-time heating of the sensor 1 up to temperatures smaller than 300° C., preferably from 110° C. to 280° C., by applying a voltage to electrodes 5 and/or 6, preferably to electrode 5.

According to the invention the metal of the first electrode 5 is selected from the group consisting of palladium, platinum, gold, ruthenium, nickel, iron, cobalt, rhodium, iridium, silver, and alloys thereof. In a preferred embodiment of the invention electrode 5 is a palladium electrode or an electrode consisting of palladium alloys with platinum, gold, ruthenium, nickel, iron, cobalt, rhodium, iridium and/or silver. The thickness of electrode 5 amounts up to 60 nm. The electrode can be deposited in a special geometry, if desired, by using e.g. dc sputtering through a metal mask which prescribe the geometry of the resulting electrode film 5. In a preferred embodiment of the invention electrode 5 consists of two large areas on both sides (diameter e.g. 2 mm) which are connected through a small path in the centre (e.g. length 1.5 mm, breadth 0.5 mm). On the large areas on both sides the contacts 8 are deposited.

The material of the semiconductor substrate 2 of the invention is selected from the group consisting of a single crystal of silicon, amorphous silicon and gallium arsenide (GaAs). Preferably a single crystal of silicon is used.

According to the invention the material of the insulating layer 3 is selected from the group consisting of $SiO_2$, $Al_2O_3$ or $Ta_2O_5$. In a preferred embodiment the insulating layer 3 is composed of two layers, one consisting of $SiO_2$ and the other consisting of $Si_3N_4$, wherein the $SiO_2$ layer is formed on the semiconductor substrate 2. The thickness of the insulating layer 3 ranges from 30 nm to 90 nm. With regard to the layer combination $SiO_2/Si_3N_4$ a ratio of about 40 nm/40 nm is preferred.

The material of the fluoride ion conducting layer 4 of the invention is selected from the group consisting of polycrystalline lanthanum fluoride ($LaF_3$), calcium fluoride ($CaF_2$) or barium fluoride ($BaF_2$). The thickness of the fluoride ion conducting layer should be in the range from 15 nm to 50 nm. In this range a favourable impedance behaviour has been found.

According to the invention the metal of the second electrode 6 is selected from the group consisting of aluminium, platinum or gold. Aluminium is preferred. The thickness of the thin metal of the second electrode 6 ranges from 300 to 2.000 nm, preferably from 400 to 600 nm.

In one preferred embodiment of the invention the hydrogen thin film sensor 1 comprises a single crystal of silicon as semiconductor substrate (2), an insulating layer (3) being composed of two layers, one consisting of $SiO_2$ and the other consisting of $Si_3N_4$, the $SiO_2$-layer being formed on the semiconductor substrate (2), a fluoride ion conducting layer (4) consisting of $LaF_3$ and a first electrode (5) consisting of palladium or its alloys with platinum, gold, ruthenium, nickel, iron, cobalt, rhodium, iridium and/or silver ($Si/SiO_2/Si_3N_4/LaF_3/Pd$). This sensor was shown to have an especially high hydrogen sensitivity which did not change with a change of the relative humidity of air (compare example 5). The lower detection limit of this sensor ranges about 2 ppm therefore being highly suitable for measuring extremly small hydrogen concentrations.

A silicon based semiconductor structure $Si/SiO_2/Si_3N_4/LaF_3/Pt$ is described from Moritz et al. In "Analytica Chimica Acta 437 (2001) 183–190" as a potentiometric oxygen sensor working at room temperature. Surprisingly, this sensor structure was now found to be useful as a hydrogen sensor. An electrochemical mechanism at the fluoride ion conducting layer/electrode 5 interface is the source for the sensor signal. Because hydrogen usually has to be detected at relatively constant oxygen concentration (e.g. in air) a lack of selectivity is not a problem for the hydrogen sensor of the present invention. In the event of fire, the hydrogen is detected with the hydrogen sensor of the present invention at such an early stage at which the oxygen concentration has not changed yet.

The thin film structure of the hydrogen sensor 1 of the invention is manufactured according to well know methods in the art. Thus, the fluoride ion conducting layer 4 can be deposited on the insulating layer 3 by termal vapour-deposition under high vacuum or high frequency sputtering.

The thin films of the first electrode 5 and the second electrode 6 can be deposited by dc sputtering, thermal vaporization or electron-beam vaporization.

The insulating layer 3 is also deposited on the semiconductor substrate 2 in a known manner, for instance by chemical vapor deposition. In the case of the preferred layer combination $SiO_2/Si_3N_4$ both layers can be deposited this way.

The invention relates in a further aspect to a hydrogen detecting device, comprising:
the described hydrogen thin film sensor 1
at least one voltage source,
a means for measuring the capacity, the photocurrent or the transistor drain source current of the hydrogen thin film sensor (1),
hardware and software for calculating the hydrogen concentration,
an alarm-notifying means alarming in recognizing that the hydrogen concentration is higher than the predetermined hydrogen reference concentration.

A still further aspect of the invention relates to a hydrogen detecting device, comprising:
the described hydrogen thin film sensor 1,
at least one voltage source,
a means for measuring the capacity, the photocurrent or the transistor drain source current of the hydrogen thin film sensor (1),
hardware and software for calculating the hydrogen concentration.

This device is also designated for the measurement of hydrogen, but does not encompass an alarm-notifying means.

The hydrogen sensor 1 of the invention can be used in different embodiments, namely as capacitive semiconductor sensor, gate region of field effect transistor (FET) or sensor based on the photoeffect in the semiconductor. To estimate the capacity the hydrogen detecting device of the invention comprises for instance a frequency generator and a lock-in amplifier. For the measurement of the photocurrent the hydrogen detecting device of the invention comprises a diode laser. Is the hydrogen detecting device of the invention used as a field effect transisitor, then a constant voltage source is included. The hydrogen detecting device comprises in all embodiments a signal control means, for instance a differential amplifier. The voltage-supply of the hydrogen detecting device of the invention does also include a voltage supply control. As an alarm-notifying means a differential amplifier can be used. Alternatively, intelligent systems can be used, which use the deviation from the long-term signal development for the alarm definition.

In accordance with these three different embodiments of using the hydrogen sensor (1) for signal detection three methods of sensing hydrogen concentrations are a further aspect of the present invention.

The invention relates to a method of sensing hydrogen concentrations using a hydrogen sensor (1) as capacitive semiconductor sensor, said method comprising the application of a d. c. voltage between the first electrode (5) and the second electrode (6) and coupling in an additional a. c. voltage, measuring the capacity by high-frequency capacity/voltage measuring technique and determining the hydrogen concentration. Additionally to the d. c. voltage an a.c. voltage, for instance of 10 kHz, is applied to the sensor. Using a frequency selective detector the capacity is, measured. Using the steepness of the capacitance/voltage curve a change in potential can be calculated from the change in capacitance.

The invention further relates to a method of sensing hydrogen concentrations using a hydrogen sensor (1), said method comprising the exposure of the semiconductor substrate (2) to modulated laser light, measuring the resulting photocurrent and determining the hydrogen concentration, The resulting photocurrent is evaluated by analogy with the capacity evaluation.

A still further aspect of the invention relates to a method of sensing hydrogen concentrations using a hydrogen sensor (1) as gate region of a field effect transistor, said method comprising the application of a constant gate voltage between the first electrode (5) and the second electrode (6), a constant drain source voltage, measuring the drain current change and determining the hydrogen concentration.

BRIEF DESCRIPRION OF THE DRAWINGS

FIG. 1 is a sectional view of the hydrogen thin film sensor 1 according to the present invention. In FIG. 1 the meanings are the following:
1 hydrogen thin film sensor
2 semiconductor substrate
3 thin film insulating layer
4 thin film fluoride ion conducting layer
5 thin metal film of the first electrode
6 thin metal film of the second electrode
7 electroconductive contacts
8 electroconductive contacts FIG. 2 shows the response behaviour of the reactivated hydrogen sensor according to example 2 of the invention with respect to different hydrogen concentrations, baseline concentration 10 ppm, right scale: hydrogen concentration in ppm.

Figure 4A:
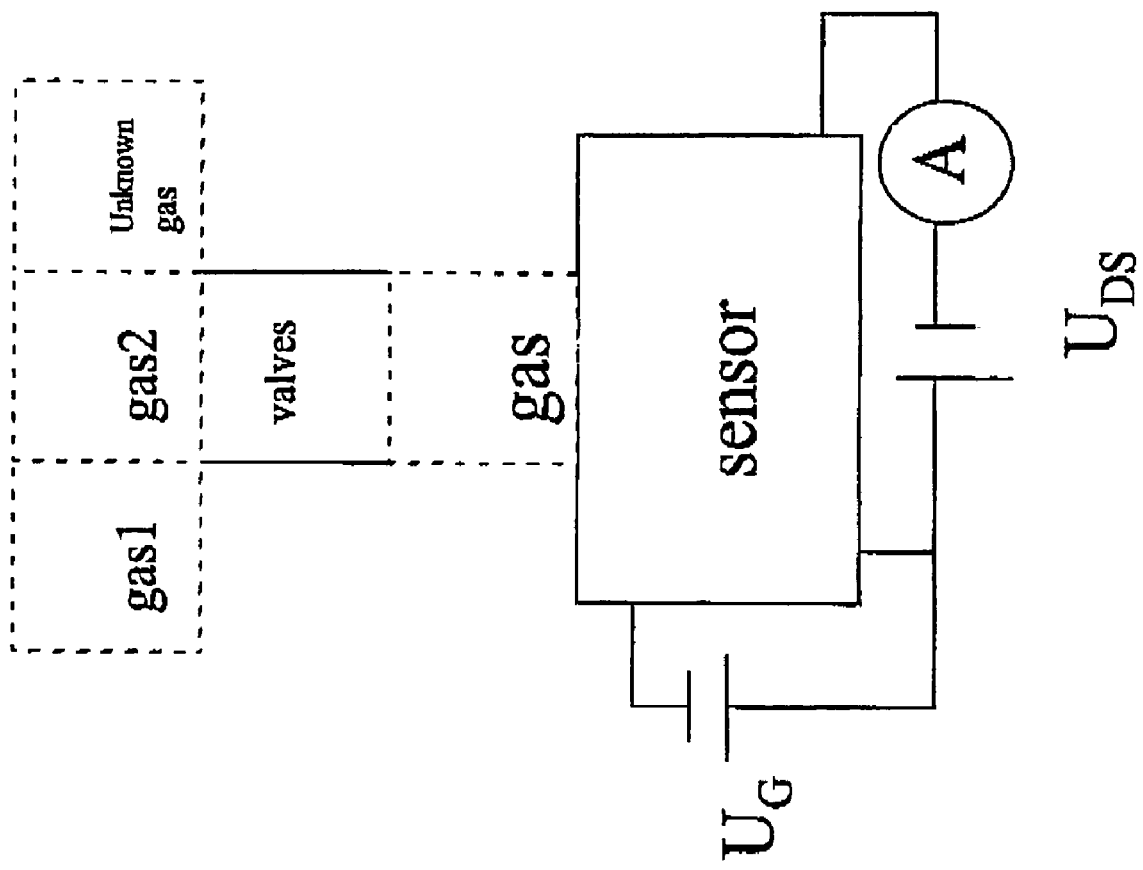
FIG. 4a shows the scheme of the hydrogen detecting device of the invention for measuring the transistor drain source current (compare embodiment 1 of the invention).

In FIG. 4a the meanings are the following:
$U_G$ gate voltage source
$U_{DS}$ drain source voltage source
A ammeter FIG. 4b shows the scheme of the hydrogen detecting device of the invention for measuring the capacity (compare embodiment 2 of the invention).

Figure 4B:
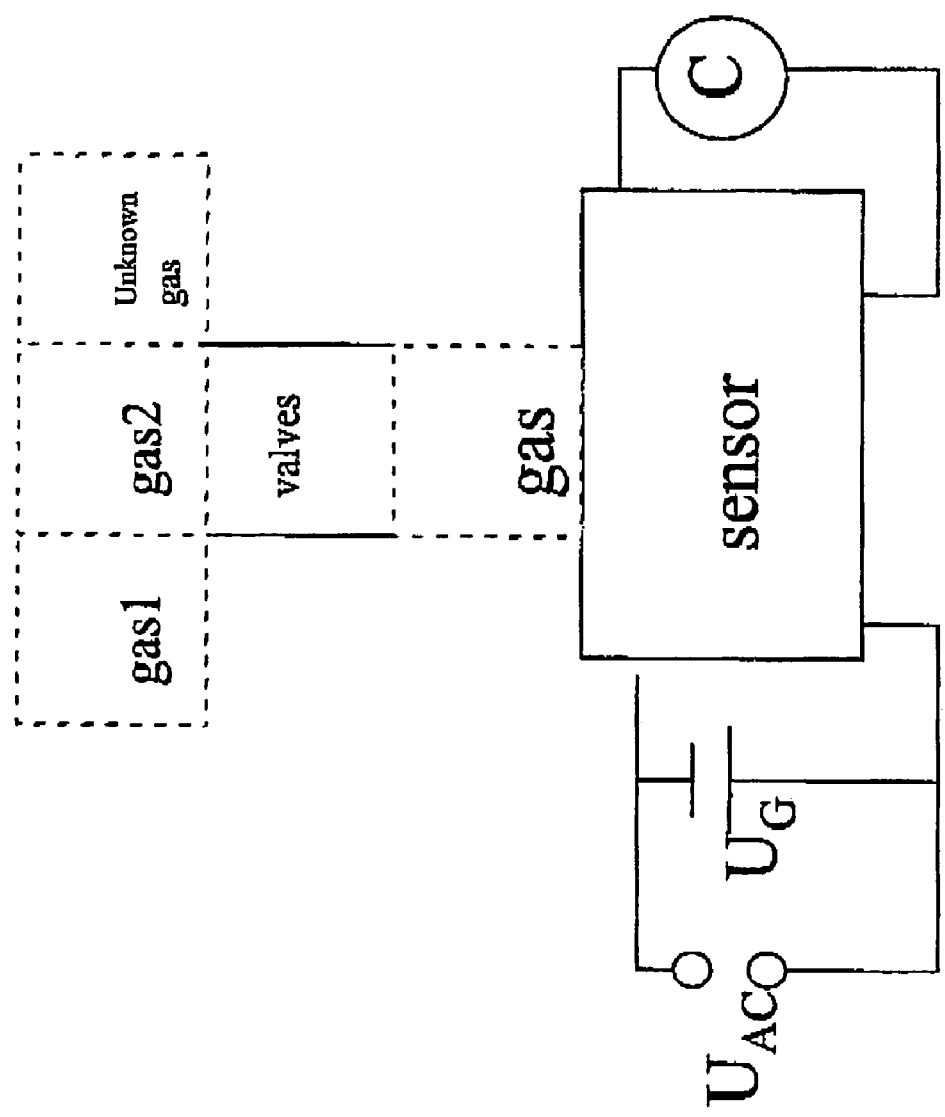

In FIG. 4b the meanings are the following:
$U_G$ gate voltage source
$U_{AC}$ AC voltage source
C capacitance meter FIG. 4c shows the scheme of the hydrogen detecting device of the invention for measuring the photocurrent (compare embodiment 3 of the invention).

Figure 4C:
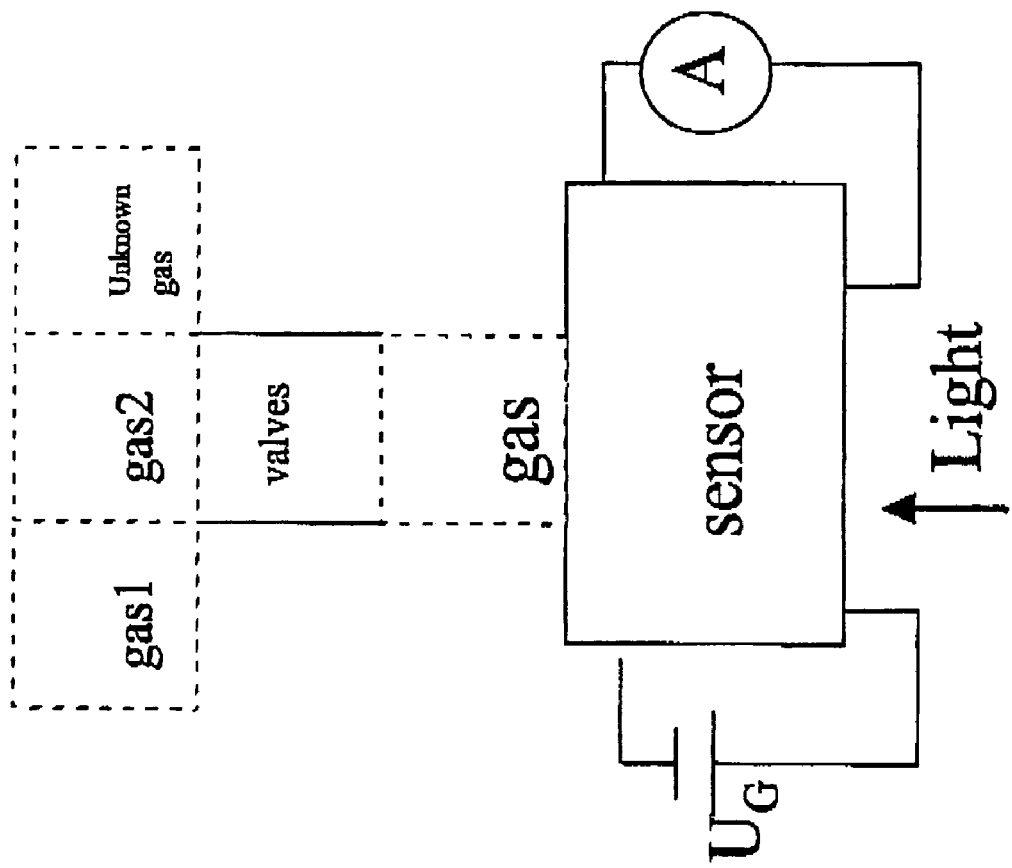

In FIG. 4c the meanings are the following:
$U_G$ gate voltage source
A ammeter

DETAILED DESCRIPTION OF THE INVENTION

Hereafter, examples and preferred embodiments of the invention will be described.

EXAMPLE 1

A sensor made of a silicon single crystal (5 mm×10 mm) and having a 40 nm SiO$_2$ layer and an additional 40 nm thick Si$_3$N$_4$ layer has been coated with LaF$_3$ under high vacuum by thermal deposition with a deposition velocity auf 0.1 nm/s. The layer thickness of the ion conducting layer amounted to 40 nm. Yet another layer comprising Pd has been deposited by DC sputtering with a deposition rate of 1 nm/s up to a layer thickness of 50 nm. Thereby a Pd area with a diameter of 2 mm has been defined using a metal mask. A back side contact has been realized through deposition of Al (500 nm).

The sensor has been characterized by means of the high frequency capacity/voltage measurement technique. During contact of the sensor with synthetic air having different hydrogen concentrations a sensitivity of 62 mV/lg P(H$_2$) has been measured at room temperature.

EXAMPLE 2

Figure 1:
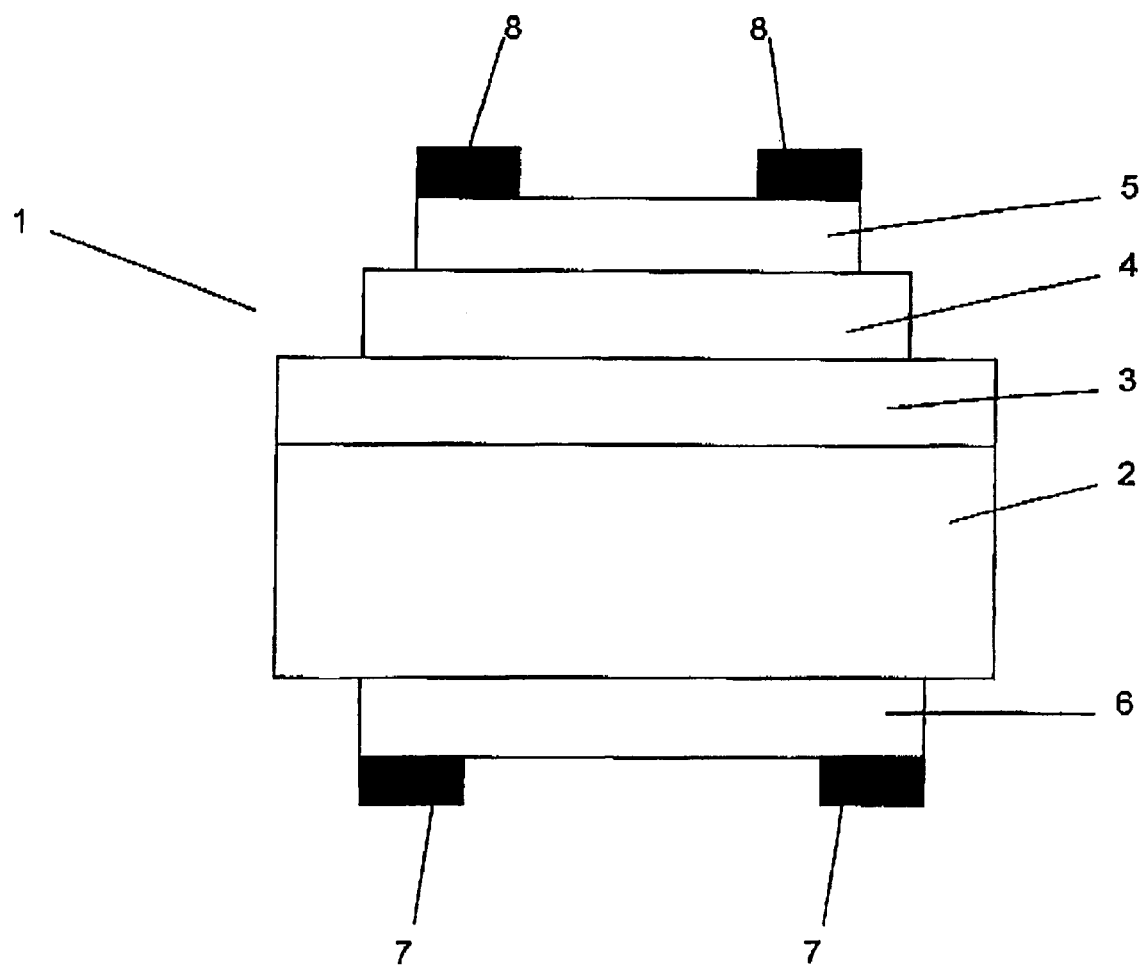
Figure 2:
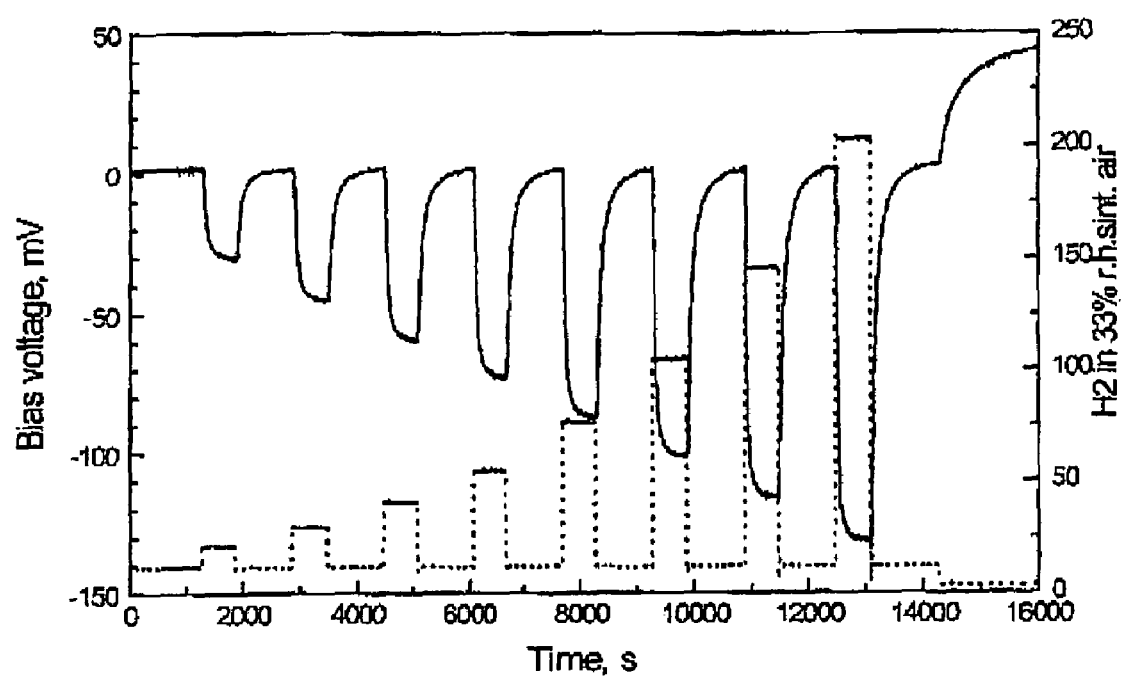

After 60 days the sensor according to embodiment 1 has been measured again as described above. Now just an extremely low response behaviour has been obtained. Afterwards the sensor has been heated-up for 10 seconds to 135° C. and subsequently measured again with respect to hydrogen sensitivity at room temperature. It produced the same behavior as described In example 1 for a new sensor. A typical response behavior is depicted in FIG. 2.

EXAMPLE 3

The hydrogen sensor described in example 2 has been tested with respect of the detection of a test fire according to the European standard EN 54 (test fire 2) [published by DIN, German Institute of Standards e.V., Ref. No. DIN EN 54-7: 2001-03; DIN EN 54-5: 2001-03; DIN EN 54-1: 1996-10; DIN EN 54-7/A1: 2002-09 and DIN EN 54-5/A1: 2002-09] in comparison to a conventional smoke detection system. The fire has been verified successfully obtaining an alarm signal already 90 sec prior to the smoke detection system.

EXAMPLE 4

Figure 3:
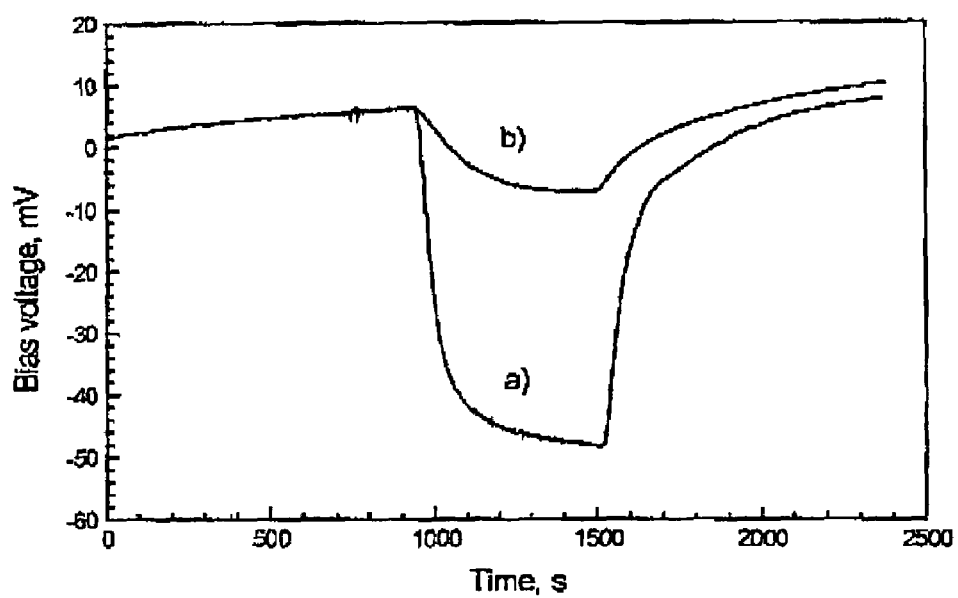
FIG. 3 shows a comparison of the sensor signals of the sensor according to example 4a of the invention with a fluoride ion conducting layer and the sensor of example 4b without a fluoride ion conducting layer; 20 ppmH$_2$.

A sensor a) according to example 1 has been fabricated. A sensor b) has been fabricated without the fluoride ion conducting layer by depositing a silicon single crystal having a 40 nm SiO$_2$ layer and an additional 40 nm thick Si$_3$N$_4$ layer with yet another layer comprising Pd up to a layer thickness of 50 nm using DC sputtering with a deposition rate of 1 nm/s. Thereby a Pd area with a diameter of 2 mm has been defined using a metal mask. A back side contact has been realized through deposition of Al (500 nm). The samples have been characterized by means of high frequency capacity/voltage measurement. During contact of the sensor with synthetic air having different hydrogen concentrations the behavior shown in FIG. 3 has been found at room temperature, which documents the advantage of the use of an additional ion conducting layer.

EXAMPLE 5

A sensor a) according to example 1 has been fabricated. A sensor b) having a Pt electrode has been fabricated by coating a silicon single crystal having a 40 nm SiO$_2$ layer and an additional 40 nm thick Si$_3$N$_4$ layer with LaF$_3$ under high vacuum by thermal deposition with a deposition velocity auf 0.1 nm/s. The layer thickness of the ion conducting layer amounted to 40 nm. Yet another layer comprising Pd has been deposited by DC sputtering with a deposition rate of 1 nm/s up to a layer thickness of 50 nm. Thereby a Pd area with a diameter of 2 mm has been defined using a metal mask. A back side contact has been realized through deposition of Al (500 nm).

Both sensors have been analyzed regarding the influence of air moisture on hydrogen sensitivity. Whereas a change of the sensitivity from 27 mV/lg p($H_2$) to 20 mV/1 g p($H_2$) with a change of the relative humidity from 33% to 80% has been observed for sensor b), the sensitivity for sensor a) remained constant.

EXAMPLE 6

A sensor according to example 1 has been fabricated.

The sensor aged for two months. 3 mm of the rear side contact of this chip 5×15 mm have been etched away. The remaining Al areas have been contacted with a temperature stable conducting adhesive and connected to a voltage source. A voltage of 17 V has been applied for 1.5 minutes. The subsequent measurement of the hydrogen sensitivity produced a result as described in example 2.

EXAMPLE 7

A sensor made of a silicon single crystal and having a 40 nm $SiO_2$ layer and an additional 40 nm thick $Si_3N_4$ layer has been coated with $LaF_3$ under high vacuum by thermal deposition with a deposition velocity auf 0.1 nm/s. The layer thickness of the ion conducting layer amounted to 40 nm. Yet another layer comprising Pd has been deposited by do sputtering with a deposition rate of 1 nm/s up to a layer thickness of 50 nm. Thereby a Pd area of 8*1 mm has been defined using a metal mask. A back side contact has been realized through deposition of Al (500 nm). The sample aged for two months, The Pd has been contacted with a temperature stable conducting adhesive at two locations at intervals of 4 mm and connected with a voltage source. A voltage of 70 V has been applied for 10 ms. The subsequent measurement of the hydrogen sensitivity produced a result as described in example 2.

Embodiment 1

Method of sensing hydrogen by using a hydrogen sensor composed of n-Si/$SiO_2$/$Si_3N_4$/$LaF_3$/Pd as prepared in example 1 as gate region of a field effect transistor (FIG. 4a).

The hydrogen sensor as described above will be used in contact to a gas 1 having a known concentration of hydrogen. A constant gate voltage and a constant drain source voltage will be applied and the resulting drain source current 1 is measured. In a second step the gas is replaced by a gas 2 of another hydrogen concentration. Using the same voltage conditions the drain source current 2 is measured. In the following the gas with an unknown hydrogen concentration will be contacted with the sensor. At the constant voltage conditions the drain source current 3 is measured.

For small concentration ranges a linear relation between the gas concentrations and the drain source current is describing the sensor behaviour. Therefore, a linear equation can be calculated using the gas concentrations 1 and 2 and the drain source currents 1 and 2. Using this equation and the drain source current 3 the unknown hydrogen concentration is calculated.

Embodiment 2

Method of sensing hydrogen by using a hydrogen sensor composed of n-Si/$SiO_2$/$Si_3N_4$/$LaF_3$/Pd prepared in example 1 as capacitive semiconductor sensor (FIG. 4b).

The hydrogen sensor as described above will be used in contact to a gas 1 having a known concentration of hydrogen. A constant gate voltage and small signal AC-voltage will be applied and the capacitance 1 of the structure is measured. In a second step the gas is replaced by a gas 2 of another hydrogen concentration. Using the same voltage conditions the capacitance 2 is measured. In the following the gas with an unknown hydrogen concentration will be contacted with the sensor. At the constant voltage conditions the capacitance 3 is measured.

For small concentration ranges a linear relation between the gas concentrations and the capacitance Is describing the sensor behaviour. Therefore, a linear equation can be calculated using the gas concentrations 1 and 2 and the capacitances 1 and 2. Using this equation and the capacitance 3 the unknown hydrogen concentration is calculated.

Embodiment 3

Method of sensing hydrogen by using a hydrogen sensor composed of n-Si/$SiO_2$/$Si_3N_4$/$LaF_3$/Pd prepared in example 1 as sensor on the basis of the photoeffect in the semiconductor (FIG. 4c).

The hydrogen sensor as described above will be used in contact to a gas 1 having a known concentration of hydrogen. A constant gate voltage will be applied and the sensor is exposed to modulated light. The resulting photocurrent 1 of the structure is measured. In a second step the gas is replaced by a gas 2 of another hydrogen concentration. Using the same voltage conditions the photocurrent 2 is measured. In the following the gas with an unknown hydrogen concentration will be contacted with the sensor. At the constant voltage conditions the photocurrent 3 is measured, For small concentration ranges a linear relation between the gas concentrations and the photocurrent is describing the sensor behaviour. Therefore, a linear equation can be calculated using the gas concentrations 1 and 2 and the photocurrents 1 and 2. Using this equation and the photocurrent 3 the unknown hydrogen concentration is calculated.

What is claimed is:

1. A hydrogen thin film sensor (1) comprising a semiconductor substrate (2), a thin film insulating layer (3), a thin film fluoride ion conducting layer (4), a thin metal film of a first electrode (5) and a thin metal film of a second electrode (6), wherein the insulating layer (3) is formed on the semiconductor substrate (2), the fluoride ion conducting layer (4) is formed on the insulating layer (3), the metal film of the first electrode (5) is formed on the fluoride ion conducting layer (4) and the metal film of the second electrode (6) is formed on the back of the semiconductor substrate (2).

2. The hydrogen sensor of claim 1, wherein the first electrode (5) or the second electrode (6) or both are accomplished as heating elements having two temperature stable and electroconductive contacts (7) or (8).

3. The hydrogen sensor of claim 1, wherein the metal of the first electrode (5) is selected from the group consisting of palladium, platinum, gold, ruthenium, nickel, iron, cobalt, rhodium, iridium, silver, and alloys thereof.

4. The hydrogen sensor of claim 1, wherein the metal of the first electrode (5) is palladium, or alloys thereof with platinum, gold, ruthenium, nickel, iron, cobalt, rhodium, iridium and/or silver.

5. The hydrogen sensor of claim 1, wherein the material of the semiconductor substrate (2) is selected from the group consisting of a single crystal of silicon, amorphons silicon and gallium arsenide (GaAs).

6. The hydrogen sensor of claim 1, wherein the material of the insulating layer (3) is selected from the group consisting of $SiO_2$, $Al_2O_3$ or $Ta_2O_5$.

7. The hydrogen sensor of claim 1, wherein the insulating layer (3) is composed of two layers one consisting of $SiO_2$ and the other consisting of $Si_3N_4$, wherein the $SiO_2$-layer is provided on the semiconductor substrate (2).

8. The hydrogen sensor of claim 1, wherein the material of the fluoride ion conducting layer (4) is selected from the group consisting of polycrystalline lanthanum fluoride ($LaF_3$), calcium fluoride ($CaF_2$) or barrium fluoride ($BaF_2$).

9. The hydrogen sensor of claim 1, wherein the thickness of the fluorid ion conducting layer (4) ranges from 15 to 50 nm.

10. The hydrogen sensor of claim 1, wherein the metal of the second electrode (6) is selected from the group consisting of aluminium, platinum or gold.

11. The hydrogen sensor (1) of claim 1 comprising a single crystal of silicon as semiconductor substrate (2), an insulating layer (3) being composed of two layers, one consisting of $SiO_2$ and the other consisting of $Si_3N_4$, the $SiO_2$-layer being formed on the semiconductor substrate (2), a fluoride ion conducting layer (4) consisting of $LaF_3$ and a first electrode (5) consisting of palladium or its alloys with platinum, gold, ruthenium, nickel, iron, cobalt, rhodium, iridium and/or silver.

12. A hydrogen detecting device comprising:
   a hydrogen thin film sensor (1) comprising a semiconductor substrate (2), a thin film insulating layer (3), a thin film fluoride ion conducting layer (4), a thin metal film of a first electrode (5) and a thin metal film of a second electrode (6), wherein the insulating layer (3) is formed on the semiconductor substrate (2), the fluoride ion conducting layer (4) is formed on the insulating layer (3), the metal film of the first electrode (5) is formed on the fluoride ion conducting layer (4) and the metal film of the second electrode (6) is formed on the back of the semiconductor substrate (2),
   at least one voltage source;
   a means for measuring the capacity, the photocurrent or the transistor drain source current of the hydrogen thin film sensor (1),
   hardware and software for calculating the hydrogen concentration,
   an alarm-notifying means alarming in recognizing that the hydrogen concentration is higher than the pre-determined hydrogen reference concentration.

13. A hydrogen detecting device comprising:
   a hydrogen thin film sensor (1) comprising a semiconductor substrate (2), a thin film insulating layer (3), a thin film fluoride ion conducting layer (4), a thin metal film of a first electrode (5) and a thin metal film of a second electrode (6), wherein the insulating layer (3) is formed on the semiconductor substrate (2), the fluoride ion conducting layer (4) is formed on the insulating layer (3), the metal film of the first electrode (5) is formed on the fluoride ion conducting layer (4) and the metal film of the second electrode (6) is formed on the back of the semiconductor substrate (2),
   at least one voltage source,
   a means for measuring the capacity, the photocurrent or the transistor drain source current of the hydrogen thin film sensor (1),
   hardware and software for calculating the hydrogen concentration.

14. A method of sensing hydrogen concentrations using a hydrogen sensor (1) of claim 1 as capacitive semiconductor sensor, said method comprising the application of a d. c. voltage between the first electrode (5) and the second electrode (6) and coupling in an additional a. c. voltage, measuring the capacity by high-frequency capacity/voltage measuring technique and determining the hydrogen concentration.

15. A method of sensing hydrogen concentrations using a hydrogen sensor (1) of claim 1 as sensor on the basis of the photoeffect in the seomiconductor, said method comprising the exposure of the semiconductor substrate (2) to modulated laser light, measuring the resulting photocurrent and determining the hydrogen concentration.

16. A method of sensing hydrogen concentrations using a hydrogen sensor (1) of claim 1 as gate region of a field effect transistor, said method comprising the application of a constant gate voltage between the first electrode (5) and the second electrode (6), a constant drain source voltage, measuring the drain current change and determining the hydrogen concentration.

17. A method of sensing hydrogen concentrations using a hydrogen sensor (1) of claim 1 as capacitive semiconductor sensor, gate region of field effect transistor or sensor based on photoeffect in the semiconductor, said method comprising the operation of the hydrogen sensor (1) at mom temperature during the measurements and the reactivation of the hydrogen sensor (1) out of the measurements by short-time heating the sensor (1) up to temperatures smaller than 300° C. by applying a voltage to the electrodes (5) and/or (6).

18. The method of claim 17, wherein the reactivation is carried out in an interval up to 7 days and for 10 μs up to 2 minutes at the most.

19. A method of reactivating a hydrogen sensor (1) of claim 1, said method comprising the short-time heating of the sensor (1) up to temperatures smaller than 300° C. by applying a voltage to the electrodes (5) and/or (6).

* * * * *